United States Patent [19]
Ribier et al.

[11] Patent Number: 5,925,364
[45] Date of Patent: Jul. 20, 1999

[54] COSMETIC OR DERMATOLOGICAL COMPOSITION COMPRISING AN OIL-IN-WATER EMULSION COMPRISING OILY GLOBULES WITH A LAMELLAR LIQUID CRYSTAL COATING

[75] Inventors: Alain Ribier; Jean-Thierry Simonnet, both of Paris; Jacques Michelet, Champlan, all of France

[73] Assignee: L'Oreal, Paris, France

[21] Appl. No.: 08/540,165

[22] Filed: Oct. 6, 1995

[30] Foreign Application Priority Data

Oct. 7, 1994 [FR] France .................................. 94 12005

[51] Int. Cl.⁶ ...................................................... A61K 7/48
[52] U.S. Cl. ............................ 424/401; 424/59; 424/450; 514/844; 514/845; 514/846; 514/938; 514/939; 514/940; 514/941; 514/942; 514/943
[58] Field of Search ....................... 424/401, 450, 424/59; 514/938–943, 844, 845, 846

[56] References Cited

U.S. PATENT DOCUMENTS

| | | | |
|---|---|---|---|
| 5,372,814 | 12/1994 | Mizushima et al. | 424/401 |
| 5,429,820 | 7/1995 | Kamitani et al. | 424/401 |

FOREIGN PATENT DOCUMENTS

| | | |
|---|---|---|
| 0 062 896 | 4/1981 | European Pat. Off. . |
| 0 084 341 | 7/1983 | European Pat. Off. . |
| 0 466 236 | 1/1992 | European Pat. Off. . |
| 2 633 515 | 1/1990 | France . |
| 2 679 788 | 2/1993 | France . |

OTHER PUBLICATIONS

T. Suzuki et al.; "Secondary Droplet Emulsion: Mechanism and effects of liquid crystal formation in O/W emulsion"; Journal of Dispersion Science and Technology; vol. 5, No. 2, 1984, pp. 119–141.

Cosmetics & Toiletries; By G.S. Kass, vol. 94, Aug. 1979, pp. 25, 26, 28 and 30, "New Techniques for Formulating Cosmetics with Lecithin".

JP 94–002223/01—Abstract.

Kosmetik; By Wilfried Jumbach, 1988, pp. 400–409.

*Primary Examiner*—Jyothsna Venkat
*Attorney, Agent, or Firm*—Oblon, Spivak, McClelland, Maier & Neustadt, P.C.

[57] ABSTRACT

The present invention relates to a cosmetic or dermatological composition comprising an emulsion of oil-in-water type formed of oily globules which are each provided with a lamellar liquid crystal coating and are dispersed in an aqueous phase. Each oily globule containing at least one lipophilic compound which is cosmetically or dermatologically active is individually coated with a monolamellar or aligolamellar layer obtained from at least one lipophilic surface-active agent, from at least one hydrophilic surface-active agent and from at least one ionic amphiphilic lipid imparting to the emulsion a pH ranging from 5.5 to 7.5, the coated oily globules having a mean diameter of less than 500 nanometers.

19 Claims, No Drawings

COSMETIC OR DERMATOLOGICAL COMPOSITION COMPRISING AN OIL-IN-WATER EMULSION COMPRISING OILY GLOBULES WITH A LAMELLAR LIQUID CRYSTAL COATING

BACKGROUND OF THE INVENTION

1. Field of the Invention

The present invention relates to a cosmetic or dermatological composition comprising an emulsion of oil-in-water type. It more particularly relates to a composition comprising an oil-in-water emulsion formed by oily globules which are provided with a lamellar liquid crystal coating and are dispersed in an aqueous phase. The invention also relates to a process for the preparation of such a composition and its application to the treatment of skin and keratinous matter.

2. DIiscussion of the Background

Numerous lipophilic active compounds have an important role to play within the field of skin care. Examples of such active agents which may be mentioned are the lipophilic vitamins A, E or F, the essential oils, sunscreen agents, long-chain alkyl esters of α-hydroxy acids, anti-inflammatory agents and agents stimulating the biosynthesis of lipids and/or of proteins.

Their use is very widespread but their effectiveness is limited by their lipophilic nature. They are, in fact, only partially absorbed by the skin and diffuse only with great difficulty into the stem cells of the stratum corneum, in which cells they are stopped by the presence of aqueous compartments in the intercorneocytic spaces.

Their introduction into oil-in-water emulsions stabilized by a monolayer of surfactants hardly improves this state of affairs, given that these emulsions are broken as soon as they are applied to the skin, releasing at the surface of the skin an oily phase containing lipophilic active agents which are very poorly absorbed for the reasons stated above.

Attempts to improve this state of affairs have been proposed in the prior art.

In JSCC 35, 45–57 (January, February 1984), Junginger et al. describe oil-in-water emulsions whose stabilization is provided by a lamellar liquid crystal three-dimensional network.

In "Secondary droplet emulsion: Contribution of liquid crystal formation to physicochemical properties and skin moisturizing effect of cosmetic emulsion" (12th International Congress IFSSC, Paris September 1992, Abstracts, Vol. I, 117–136), Suzuki et al. describe these oil-in-water emulsions as forming superstructures ("secondary droplets"), aggregates of oily droplets coated with liquid crystal lamellae. These authors show that the existence of these superstructures is dependent on the presence of fatty alcohol.

The main qualities of this type of emulsion are stability with respect to the release of oil and a skin moisturizing effect. However, this type of emulsion has disadvantages. It is, in fact, necessary to use large amounts of surfactant in order to constitute the three-dimensional network, thereby increasing the risks of intolerance on the part of the user, which is reflected in a long "soaping" (persistence of a white color) during the application of such compositions to the skin. In addition, the oil dispersion is coarse and heterogeneous, and the oil is more sequestered by the three-dimensional network than genuinely dispersed in the form of individualized oil microdroplets. The oil droplets generated by this type of emulsion have a mean size which is very much greater than the intercorneocytic spaces that they have to cross and very much greater than the hair pores into which they have to be taken up, which contributes towards explaining the very partial penetration into skin and hair of the fatty phase and of the active agents which are dissolved therein.

Also known is the article by Dahms in Cosmetics and Toiletries, Vol. 101 November 1986, which describes emulsions having the same characteristics and, thus, the same drawbacks.

It is thus observed that the need still remained in the prior art for emulsions allowing an improved penetration of cosmetic or dermatological compositions into the skin and hair.

The Applicant has now discovered a new emulsion which allows this objective to be achieved.

SUMMARY OF THE INVENTION

Accordingly, one object of this Application is to provide a novel cosmetic or dermatological composition comprising an emulsion of oil-in-water type formed of oily globules which are each provided with a lamellar liquid crystal coating and are dispersed in an aqueous phase, characterized in that each oily globule containing at least one lipophilic compound which is cosmetically or dermatologically active is individually coated with a monolamellar or oligolamellar layer obtained from at least one lipophilic surface-active agent, from at least one hydrophilic surface-active agent, and from at least one ionic amphiphilic lipid imparting to the emulsion a pH ranging from 5.5 to 7.5, the coated oily globules having a mean diameter of less than 500 nanometers.

Another object of the present invention is an emulsion of the oil-in-water type formed of oily globules which are each provided with a lamellar liquid crystal coating and are dispersed in an aqueous phase, characterized in that each oily globule is individually coated with a monolamellar or oligolamellar layer obtained from at least one lipophilic surface-active agent, from at least one hydrophilic surface-active agent, and from at least one ionic amphiphilic lipid imparting to the emulsion a pH ranging from 5.5 to 7.5, the coated oily globules having a mean diameter of less than 500 nanometers.

In the context of the present invention, "lipophilic active compound" is understood to refer to the active compound per se when it is itself an oil or alternatively, if it is not, the active compound dissolved in an oil. Oils which may be used are oils conventionally used as vehicles in cosmetic compositions, such as for example short-chain fatty acid triglycerides, silicone oils and the like.

The invention makes available particularly stable emulsions having fatty phase droplets of extremely small size which are coated with an extremely fine mono- or oligolamellar layer. "Oligolamellar layer" is understood to refer to a layer comprising from 2 to 5 lipid lamellae. The mean size of the coated oily globules is less than 500 nanometers and preferably less than 200 nanometers for the formulations of milk or cream type, and it is less than 80 nanometers for transparent or opalescent formulations. On account of the small size of the oily globules, their penetration into the intercorneocytic spaces, which are of comparable size, is greatly facilitated.

The active agent contained in or constituted by the oily globule may consequently be transported and delivered to the skin or hair at the site where its action will be the most effective.

According to a preferred embodiment of the invention, the lipophilic surface-active agent, the hydrophilic surface-active agent each contain at least one saturated fatty chain having more than 12 carbon atoms approximately. Even more preferably, this fatty chain contains from 16 to 22 carbon atoms.

According to another preferred embodiment of the invention, the lipophilic surface-active agent has an HLB between approximately 2 and approximately 5. As is well known to those skilled in the art, "HLB" (Hydrophilic-Lipophilic Balance) is understood to refer to the equilibrium between the size and force of the hydrophilic group and the size and force of the lipophilic group of the surface-active agent.

Another object of the invention is to provide a novel process for the preparation of the cosmetic or dermatological compositions and the oil-in-water emulsion described above.

DETAILED DESCRIPTION OF THE PREFERRED EMBODIMENTS

Examples of such lipophilic surface-active agents are sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 oxyethylene units), glyceryl mono- and dibehenate and pentaerythritol tetrastearate.

The hydrophilic surface-active agent preferably has an HLB between approximately 8 and approximately 12.

The following compounds may be mentioned as examples of such hydrophilic surfactants: polyoxyethylenated sorbitan monostearate 4 EO, polyoxyethylenated sorbitan tristearate 20 EO, polyoxyethylenated monostearate 8 EO, hexaglyceryl monostearate, polyoxyethylenated monostearate 10 EO and polyoxyethylenated distearate 12 EO, and polyoxyethylenated methylglucose distearate 20 EO.

The ionic amphiphilic lipid used within the context of the present invention is preferably chosen from the group comprising neutralized anionic lipids, amphoteric lipids and alkylsulphonic derivatives.

The neutralized anionic lipids are chosen, in particular, from:

alkali metal salts of dicetyl phosphate, and in particular the sodium and potassium salts;

the alkali metal salts of dimyristyl phosphate, and in particular the sodium and potassium salts;

the alkali metal salts of cholesteryl sulphate, and in particular the sodium salt;

the alkali metal salts of cholesteryl phosphate, and in particular the sodium salt;

the monosodium and disodium salts of acylglutamic acids, and in particular the monosodium and disodium salts of N-stearoylglutamic acid;

the sodium salt of phosphatidic acid.

The amphoteric lipids are chosen in particular from phospholipids and especially phosphatidylethanolamine from pure soya.

The alkylsulphonic derivatives are advantageously the compounds of formula:

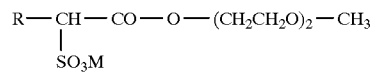

in which R represents the radicals $C_{16}H_{33}$ and $C_{18}H_{37}$, taken as a mixture or separately, and M is an alkali metal, preferably sodium.

The coating according to the invention of the oily globules preferably requires the use of a total amount of hydrophilic surface-active agent, of lipophilic surface-active agent and of ionic amphiphilic lipid between approximately 2% and approximately 6% by weight relative to the total weight of the composition. Even more preferably, this amount is between 3% and 4%. The relative amounts of lipophilic surfactant, hydrophilic surfactant and ionic amphiphilic lipid preferably vary within the following respective ranges:

35–55%/25–40%/15–35% by weight relative to their total weight.

The fatty phase, that is to say the coated oily droplets, preferably represents 5 to 50% by weight relative to the total weight of the composition. Even more preferably, this percentage is between 10 and 40. The oil/water ratio is preferably less than or equal to 1.

The weight ratio of the oily globules to the elements constituting the coating is preferably from 2 to 13, more preferably from 6 to 8, even more preferably this ratio is approximately equal to 7.

When the compositions according to the invention are used for the cosmetic treatment of the skin or for dermatological purposes, the active agent contained in the oily phase is, for example, chosen from antioxidants, free radical scavengers, moisturizing agents, melanoregulators, tanning accelerators, depigmenting agents, skin-coloring agents, liporegulators, thinning agents, anti-acne agents, antiseborrhoeic agents, anti-ageing agents, anti-wrinkle agents, anti-UV agents, keratolytic agents, anti-inflammatory agents, refreshing agents, cicatrizing agents, vascular protectors, antibacterial agents, antifungal agents, antiperspirants, deodorants, skin conditioners, immunomodulators, nutrients and essential oils and perfumes.

When the compositions according to the invention are used for the cosmetic treatment of keratinous matter, the active agent contained in the oily phase is, for example, chosen from melanoregulators, liporegulators, antiseborrhoeic agents, anti-ageing agents, anti-UV agents, keratolytic agents, antibacterial agents, antifungal agents, anti-dandruff agents, agents for combating hair loss, hair dyes, hair bleaches, reducing agents for permanent waves, hair conditioners and nutrients.

The following compounds may be mentioned as examples of lipophilic active agents for the treatment of the skin and/or hair, which may be used within the context of the present invention:

D-α-tocopherol, DL-α-tocopherol, D-α-tocopheryl acetate, DL-α-tocopheryl acetate, ascorbyl palmitate, glycerides of vitamin F, D-vitamins and especially vitamin $D_2$ and vitamin $D_3$, retinol, retinol esters (retinol palmitate and retinol propionate), β-carotene, D-panthenol, farnesol, farnesyl acetate, oils rich in essential fatty acids and especially jojoba oil and blackcurrant oil, 5-n-octanoylsalicylic acid, salicylic acid, alkyl esters of α-hydroxy acids such as citric acid, lactic acid and glycolic acid, asiatic acid and madecassic acid, asiaticoside, whole extract of Centella asiatica, β-glycyrrhetinic acid, α-bisabolol, ceramides and especially 2-oleoylamino-1,3-octadecane, phytanetriol, sphingomyelin from milk, phospholipids of marine origin which are rich in polyunsaturated essential acids, ethoxyquine, extract of romarin, extract of balm, quercetin, extract of dried microalgae (algoxan red from Algatec), essential oil of bergamot, octyl methoxycinnamate (Parsol MCX—Givaudan-Roure), butyl-methoxydibenzoylmethane (Parsol 1789—Givaudan-Roure), octyl triazone (Uvinul T150—BASF), yellow, brown, black and red iron oxides, titanium oxides which may be provided in micrometric or nanometric form or in coated (perfluoroalkyl) form, 3,5-di-tert-butyl-4-hydroxybenzylidene-3-camphor, 2-benzotriazol-2-yl-4-methyl-6-[3-[1,3,3,3-tetramethyl-1-[(trimethylsilyl)oxy]disiloxanyl]-2-methylpropyl]phenol, perfluoro oil (perfluorodecalin and perfluorooctyl bromide) and hyperoxygenated corn oil (Epaline 100 marketed by the company Carilene).

Moreover, the Applicant has found that the incorporation of nanometer-sized pigments, and especially of nanotitaniums, into the compositions of the invention made it possible to obtain sun protection compositions which have a higher protection factor (SPF) than that of compositions not containing the globules according to the invention. The term nanometer-sized should be understood to mean a particle size of less than 200 nanometers, and in particular of the order of 10 to 50 nanometers.

The compositions according to the present invention may additionally contain, in the aqueous phase, one or more free or encapsulated, cosmetically or dermatologically active hydrophilic compounds.

It is possible to use hydrophilic active agents which are conventionally used, such as antioxidants, free radical scavengers, moisturizing agents, melanoregulators, tanning accelerators, depigmenting agents, skin-coloring agents, liporegulators, thinning agents, anti-acne agents, antiseborrhoeic agents, anti-ageing agents, anti-wrinkle agents, anti-UV agents (benzene-1,4-[di(3-methylidenecamphor-10-sulphonic)]acid), keratolytic agents, anti-inflammatory agents, refreshing agents, cicatrizing agents, vascular protectors, antibacterial agents, antifungal agents, antiperspirants, deodorants, skin and hair conditioners, immunomodulators, nutrients, anti-dandruff agents, agents for combating hair loss, hair dyes, hair bleaches, reducing agents for permanent waves and essential oils and perfumes.

As hydrophilic active agent, there may in particular be used a short-chain ($C_1$ to $C_6$) alcohol such as ethanol, a polyol such as a glycol, and especially 1,3-butylene glycol, propylene glycol, dipropylene glycol, isoprene glycol or hexylene glycol, glycerol, polyglycerol and sorbitol.

When it is provided in the encapsulated state, this compound may be incorporated into a lipid vesicle obtained from ionic or nonionic lipids or from a mixture of the two. It may also be incorporated into lipid nanoparticles such as nanospheres, nanosponges or nanocapsules.

The incorporation of lipid vesicles into the compositions of the invention is particularly advantageous because of the complementary nature and the good compatibility of these two types of vehicles, namely, on the one hand, oily globules containing lipophilic active agents, with a preferred mean size in the region of 200 nm which are delimited by their lamellar liquid crystal coating, and, on the other hand, lipid vesicles having an aqueous core containing hydrophilic active agents, with a preferred mean size in the region of 200 nm, which are delimited by their lamellar wall.

The inventors have furthermore observed that the lipid vesicles based on unsaturated natural ionic lipids, which are particularly sensitive to the presence of surfactants in the aqueous phase (which is the case in the standard emulsions) and to the presence of peroxides, were conserved particularly well in the compositions of the invention based on surfactants containing saturated fatty chains having more than 12 carbon atoms.

The compositions of the invention may also contain, in the aqueous phase, various complementary additives such as preserving agents, sequestering agents and gelling agents.

Depending on the viscosity which it is desired to obtain for the final composition, one or more gelling agents may or may not be added. Thus, when it is desired to obtain compositions in the form of sera, no gelling agents are introduced into the composition.

The compositions of the invention may also contain, in the fatty phase, various complementary additives such as oils, waxes or gums having, for example, emollient or lubricating properties.

The compositions are most often provided in milk, cream or gel form, other modes of presentation not being excluded. They are transparent or translucid when the particle size is less than 80 nm.

Another object of the invention is to provide a novel process for the preparation of the compositions described above, characterized in that, in a first step, the fatty phase comprising the lipophilic surfactant, the hydrophilic surfactant, the ionic amphiphilic lipid, the cosmetically or dermatologically active compound and the aqueous phase are mixed and, in a second step, the mixture obtained is subjected to a homogenization based on the principle of cavitation. Homogenization based on the principle of cavitation is well known to those skilled in the art.

In the first step, the mixture is subjected to conventional stirring, for example in a homogenizer rotating at a rate approximately between 500 and 5000 rev/min for a time approximately between 10 and 60 min and at a temperature approximately between 20 and 95° C.

The homogenization based on the principle of cavitation in the second step is a key step of the process according to the invention. This homogenization results from the cavitation phenomenon created and maintained within the mixture, which mixture is then in liquid form, in movement at a linear velocity of at least 100 m/s.

It may be performed by using a high pressure homogenizer operating at pressures approximately between 200 and 1500 bar. The principle of the use of this type of homogenizer is well known to a person skilled in the art. The process is performed by successive passages, generally from 2 to 10 passages, at the selected pressure, the mixture being returned to normal pressure between each passage.

The homogenization of the second step may also be obtained under the action of ultrasound or alternatively by the use of homogenizers equipped with a head of rotor-stator type.

When the aqueous phase contains hydrophilic active agents which are cosmetically or dermatologically active, if the latter are introduced in the free state they are introduced in the first step. If, on the contrary, they are introduced in the encapsulated state, they must be introduced in a subsequent third step. In this case, they are introduced by a simple mixing.

The invention will now be described more completely, in its aims and its characteristics, using the examples which are to follow.

In the examples, the process is performed using the following procedure:

The oily phase A1 and the aqueous phase B are heated separately to a temperature of 80° C.

Phase B is poured onto phase A1, with stirring of 4000 rev/min provided by a Moritz homogenizer of type Turbo Lab 2100, and these stirring and temperature conditions are maintained for 30 minutes.

The mixture is then introduced into a Soavi high pressure homogenizer of type OBL, which is adjusted to a pressure of 500 bar for Examples 1 to 7, and at a pressure of 1200 bar for Example 8, for 3 successive passages.

A stabilized oil-in-water emulsion is thus obtained, the oily globules of which have a mean size of less than 200 nm and a polydispersity index of less than 0.1, as measured by a laser granulometer of type AMTECH BI 90.

The emulsion is subsequently cooled to bring it back to room temperature, which takes approximately 60 minutes. The oily phase A2 is then added to the emulsion and the whole mixture is subjected to the stirring given by the Turbo Lab 2100 at a rate of 3000 rev/min for 10 min, after which this premixture is introduced into the Soavi-OBL, which is adjusted to a pressure of 350 bar, for a further 2 passages.

After each of these two passages, the product is recooled to room temperature.

The phase C, when present, is added to this emulsion A1+B+A2, and the whole mixture is stirred using a Rayneri homogenizer equipped with a turbine of deflocculent type, at a rate of 2500 rev/min for 30 min at room temperature.

Other features of the invention will become apparent in the course of the following descriptions of exemplary embodiments which are given for illustration of the invention and are not intended to be limiting thereof.

EXAMPLES

Example 1
Moisturizing Milk for the Body

| Phase A1: | |
|---|---|
| Sucrose distearate marketed by the company Stéarinerie Dubois | 1.5% |
| Oxyethylenated sorbitan stearate containing 4 mol of ethylene oxide, marketed under the name "TWEEN 61" by the company ICI | 1% |
| Disodium salt of N-stearoylglutamic acid, marketed by the company Ajinomoto under the name "ACYLGLUTAMATE HS 21" | 0.75% |
| Stearyl heptanoate | 3% |
| Vaseline codex | 1% |
| Volatile silicone oil | 2% |
| Jojoba oil | 2% |
| Vitamin E acetate | 0.5% |
| Phase A2: | |
| Silicone gum marketed by the company Dow Corning under the name "Q$_2$-1403 FLUID" | 2% |
| Propylparaben | 0.1% |
| Perfume | 0.3% |
| Phase B: | |
| Glycerol | 5% |
| Methylparaben | 0.3% |
| Propylene glycol | 3% |
| Demineralized water | qs 100% |
| Phase C: | |
| Mixture of carboxyvinyl polymers marketed under the name "CARBOPOL 940" by the company Goodrich | 0.3% |
| Triethanolamine | 0.1% |
| Demineralized water | 9.6% |

The mean size of the oil globules of the stabilized emulsion is 160 nm with a polydispersity index of 0.07.

Example 2
Facial Anti-Ageing Day Cream

| Phase A1: | |
|---|---|
| Diglyceryl distearate marketed by the company Nihon Emulsion under the reference "EMALEX PSGA" | 1.75% |
| Polyoxyethylenated methylglucose distearate 20 EO, marketed by the company Amerchol under the name "GLUCAM E 20 DISTEARATE" | 1.15% |
| Sodium dicetyl phosphate | 0.75% |
| Stearyl heptanoate | 4% |
| Vaseline codex | 1.5% |
| Avocado oil | 3.2% |
| Jojoba oil | 3% |
| Volatile silicone oil | 2.7% |
| Vitamin E acetate | 1% |
| Natural D-α-tocopherol marketed by the company Henkel under the name "COPHEROL 1300" | 1% |
| Vitamin F glycerides | 3% |
| Retinol palmitate marketed by Fluka, assayed at 1500 IU/mg | 0.5% |
| Phase A2: | |
| Silicone gum marketed by Dow Corning under the name "Q$_2$-1403 FLUID" | 3% |
| Propylparaben | 0.2% |
| Perfume | 0.3% |
| Phase B: | |
| Glycerol | 3% |
| Hydroxyproline | 1% |
| D-Panthenol | 1% |
| Methylparaben | 0.3% |
| Demineralized water | qs 100% |
| Phase C: | |
| Mixture of carboxyvinyl polymers marketed under the name "CARBOPOL 940" by the company Goodrich | 0.4% |
| Demineralized water | 9.5% |
| Triethanolamine | 0.25% |

The mean size of the oil globules of the stabilized emulsion is 190 nm with a polydispersity index of 0.07.

A smooth white cream is obtained, which feels fresh, supple and very comfortable on application.

Example 3
Night Cream Containing Nonionic Liposomes for Stressed and Disorganized Skins

| Phase A1: | |
|---|---|
| Tetraglyceryl tristearate marketed by the company Nikkol under the name "TETRAGLYN 3 S" | 2% |
| Oxyethylenated sorbitan stearate containing 4 mol of ethylene oxide, marketed under the name "TWEEN 61" by the company ICI | 1.4% |
| Sodium dicetyl phosphate | 1% |
| Stearyl heptanoate | 5.5% |
| Vaseline codex | 2.1% |
| Macadamia oil | 4.5% |
| Apricot almond oil | 3.5% |
| Volatile silicone oil | 3.7% |
| Vitamin E acetate | 1% |
| Vitamin F glycerides | 3% |
| Natural D-α-tocopherol marketed by the company Henkel under the reference "COPHEROL 1300" | 0.5% |
| Phase A2: | |
| Silicone gum marketed by Dow Corning | 4% |

-continued

| | |
|---|---|
| under the name "Q₂-1403 FLUID" | |
| Propylparaben | 0.1% |
| Perfume | 0.3% |
| Phase B: | |
| Methylparaben | 0.3% |
| Demineralized water | qs 100% |
| Phase C: This is broken down here into two phases C1 and C2 | |
| Phase C1: Vesicle phase | |
| Tetraglyceryl tristearate marketed by Nikkol under the name "TETRAGLYN 3 S" | 0.46% |
| Cholesterol | 0.46% |
| N-Stearoylglutamic acid monosodium salt marketed under the name "ACYLGLUTAMATE HS 11" by the company Ajinomoto | 0.08% |
| Glycerol | 3% |
| Hydroxyproline | 1% |
| Demineralized water | 5% |

This phase is prepared in the following way:

The 3 lipids constituting the lipid wall of the vesicles are heated to the temperature of 115° C. which is necessary and sufficient to achieve the co-fusion thereof. A transparent liquid mixture is thus obtained, which is cooled to a temperature of 90° C.

The remainder of the aqueous phase C1 is then added in order to perform the hydration of the lipid mixture at this same temperature of 90° C. by slow stirring for 60 minutes. This mixture is cooled to 60° C. and is then introduced into the Soavi homogenizer of type OBL, which is adjusted to a pressure of 500 bar, for 3 successive passages.

| Phase C2: | |
|---|---|
| Mixture of carboxyvinyl polymers marketed under the name "CARBOPOL 940" by the company Goodrich | 0.3% |
| Triethanolamine | 0.1% |
| Demineralized water | 9.6% |

Phase C1, cooled to room temperature, is mixed with the gelified phase C2 in order to constitute the phase C.

The mean size of the oil globules of the stabilized emulsion is 180 nm and the polydispersity index is 0.07.

A smooth and shiny white cream which feels very comfortable after application is obtained.

Example 4

Day Cream Containing Liposomes, for Sensitive, Stressed and Disorganized Skins

| Phase A1: | |
|---|---|
| Diglyceryl monostearate marketed by the company Nikkol under the reference "DGMS" | 1.5% |
| Polyoxyethylenated monostearate 8-EO marketed by ICI under the name Myrj 45 | 1% |
| Monosodium salt of N-stearoylglutamic acid, marketed by the company Ajinomoto under the name "ACYLGLUTAMATE HS 11" | 0.75% |
| Stearyl heptanoate | 4% |
| Vaseline codex | 1% |
| Volatile silicone | 3.2% |
| Jojoba oil | 3% |
| Sweet almond oil | 2.7% |
| Vitamin E acetate | 0.5% |
| Natural D-α-tocopherol marketed by the company Henkel under the name | 1% |

-continued

| | |
|---|---|
| "COPHEROL 1300" | |
| Octyl methoxycinnamate marketed by the company Givaudan under the name "PARSOL MCX" | 2% |
| Butylmethoxydibenzoylmethane marketed by the company Givaudan under the name "PARSOL 1789" | 0.5% |
| Phase A2: | |
| Silicone gum marketed by the company Dow Corning under the name "Q₂-1403 FLUID" | 3% |
| Preservative | 0.1% |
| Perfume | 0.3% |
| Phase B: | |
| Preservatives | 0.1% |
| Perfume | 0.3% |
| Triethanolamine | 0.35% |
| Demineralized water | qs 100% |
| Phase C: This is composed of two phases C1 and C2: | |
| Phase C1: Vesicle phase | |
| Mixture of phospholipids in a water/alaohol mixture marketed under the name "NATIPIDE II" by the company Natterman Phospholipid | 5% |
| Glycerol | 3% |
| Demineralized water | 9% |

This phase is prepared by dispersing NATIPIDE II in the remainder of the aqueous phase, at room temperature, using a magnetic stirring bar rotating at a rate of 300 rev/min for 30 min.

| Phase C2: | |
|---|---|
| Carboxyvinyl polymer marketed by the company SIGMA under the name "SYNTHALEN K" | 0.5% |
| Demineralized water | 9.3% |
| Triethanolamine | 0.2% |

Phase C1 is then mixed with phase C2 in order to constitute phase C.

The mean size of the oil globules of the stabilized emulsion is 160 nm and the polydispersity index is 0.08.

A smooth, white cream with a fine, non-greasy texture and a very comfortable feel is obtained.

Example 5

Perfumed Body Milk

| Phase A: | |
|---|---|
| Diglyceryl monostearate marketed by the company Nikkol under the name DGMS | 1.5% |
| Oxyethylenated sorbitan stearate containing 4 mol of ethylene oxide, marketed by the company ICI under the name "TWEEN 61" | |
| Disodium salt of N-stearoylglutamic acid, marketed by the company Ajinomoto under the name "ACYLGLUTAMATE HS 21" | 0.75% |
| Stearyl heptanoate | 2% |
| Sesame oil | 6% |
| Volatile silicone oil | 2% |
| Essential oil of bergamot (Bergaptene-free) | 8% |
| Phase B: | |
| Silicone gum marketed by the company | 2% |

-continued

| | |
|---|---|
| Dow Corning under the name "Q$_2$-1403 FLUID" | |
| Preservative | 0.1% |
| Phase C: | |
| Glycerol | 3% |
| Propylene glycol | 5% |
| Preservatives | 0.3% |
| Demineralized water | qs 100% |

The average size of the oil globules of the stabilized emulsion is 130 nm with a polydispersity index of 0.06.

A very fluid white milk is obtained which may be sprayed using a pump-bottle dispenser. This milk has long-lasting perfuming properties.

Example 6

Tinted Cream Intended for Fair Skins

| | |
|---|---|
| Phase A1: | |
| Sucrose distearate marketed by the company Stearinerie Dubois | 2% |
| Oxyethylenated sorbitan stearate containing 4 mol of ethylene oxide, marketed by the company ICI under the name "TWEEN 61" | 1.35% |
| Sodium dicetyl phosphate | 1% |
| Stearyl heptanoate | 5.5% |
| Vaseline codex | 2.1% |
| Volatile silicone oil | 6% |
| Avocado oil | 4% |
| Jojoba oil | 4% |
| DL-α-Tocopheryl acetate | 0.5% |
| Phase A2 | |
| Silicone gum marketed by the company Dow coming under the name "Q$_2$-1403 FLUID" | 4% |
| Propylparaben | 0.1% |
| Perfume | 0.3% |
| Phase B: | |
| Methylparaben | 0.1% |
| Germal II | 0.3% |
| Pentasodium salt of amino(trimethylene-phosphonic) acid, marketed by the company Monsanto under the name "Dequest 2046" (sequestering agent) | 0.05% |
| Glycerol | |
| Demineralized water | 45% |
| Phase C: | |
| Saponite marketed by the company Vanderbilt under the name "VEEGUM" | 0.35% |
| Yellow iron oxides | 0.77% |
| Brown iron oxides | 0.77% |
| Black iron oxides | 0.35% |
| Titanium dioxides | 5.11% |
| Xanthan gum marketed by the company Kelco under the name "KELTROL T" | 0.2% |
| Demineralized water | qs 100% |

The average size of the coated oil globules is 180 nm with a polydispersity index of 0.08.

A smooth tinted cream is thus obtained, which very uniformly covers the imperfections in facial color tone.

Example 7

Sun Protection Cream with a High Protection Factor

| | |
|---|---|
| Phase A1: | |
| Sucrose distearate marketed by the company Stearinerie Dubois | 1.5% |
| Oxyethylenated sorbitan stearate containing 4 mol of ethylene oxide, marketed by the company ICI under the name "TWEEN 61" | |
| Disodium salt of N-stearoylglutamic acid, marketed by the company Ajinomoto under the name "ACYLGLUTAMATE HS 21" | 0.85% |
| Stearyl heptanoate | 5.5% |
| Vaseline codex | 2.1% |
| Avocado Oil | 4% |
| Jojoba Oil | 4% |
| DL-α-Tocopheryl acetate | 0.5% |
| Octyl methoxycinnamate marketed by the company Givaudan Roure under the name "PARSOL MCX" | 2% |
| Butyl methoxycinnamate marketed by the company Givaudan Roure under the name "PARSOL 1789" | 0.5% |
| Ethoxyquine | 0.03% |
| Phase A2: | |
| Nanometric titanium dioxide marketed by the company Tayca under the name "MT 100 T" | 10% |
| Dodecamethylcyclohexasiloxane marketed by the company Hercules | 10% |
| Silicone gum marketed by the company Dow Corning under the name "Q$_2$-1403 Fluid" | 4% |
| Phase B: | |
| Preservatives | 0.4% |
| Sequestering agent | 0.05% |
| Glycerol | 3.0% |
| Demineralized water | 42.67% |
| Phase C: | |
| Mixture of carboxyvinyl polymers marketed by the company Goodrich under the name "CARBOPOL 940" | 0.3% |
| Triethanolamine | 0.1% |
| Demineralized water | qs 100% |

The average size of the coated oil globules is 170 nm with a polydispersity index of 0.12.

A smooth white cream is obtained, which has a better sun protection factor than the same composition in which the oily globules are not coated according to the invention.

Example 8

Transparent Composition for Moisturizing the Skin

| | |
|---|---|
| Phase A: | |
| Diglyceryl distearate marketed by the company Nihon Emulsion under the reference "EMALEX PSGA" | 2.15% |
| Polyoxyethylenated methylglucose distearate 20 EO, marketed by the company Amerchol under the name "GLUCAM E 20 DISTEARATE" | 1.15% |
| Disodium salt of N-stearoylglutamic acid, marketed by the company Ajinomoto under the name "ACYLGLUTAMATE HS 21" | 0.85% |
| Stearyl heptanoate | 2% |
| Avocado oil | 6% |
| Jojoba oil | 6% |
| Volatile silicone oil | 4% |
| Vitamin E acetate | 1% |
| Stearic acid | 0.6% |

-continued

Phase B:

| | |
|---|---|
| Glycerol | 5% |
| Methylparaben | 0.3% |
| Ethanol | 15% |
| Demineralized water | qs 100% |

A transparent composition is obtained, in which the average size of the oil globules of the stabilized emulsion is 50 nm with a polydispersity index of 0.09.

This application is based upon French Application No. 94-12005 filed in the National Institute of Industrial Property (INPI) on Oct. 7, 1994, the entire contents of which are hereby incorporated by reference.

What is claimed as new and is desired to be secured by Letters Patent of the United States is:

1. Cosmetic or dermatological composition comprising an oil-in-water emulsion comprising oily globules which are each provided with a lamellar liquid crystal coating and are dispersed in an aqueous phase, wherein each oily globule containing at least one lipophilic compound which is cosmetically or dermatologically active is individually coated with a monolamellar or oligolamellar layer obtained from at least one lipophilic surface-active agent, from at least one hydrophilic surface-active agent and from at least one ionic amphiphilic lipid imparting to the emulsion a pH ranging from 5.5 to 7.5, the coated oily globules having a mean diameter of less than 500 nanometers;

wherein the lipophilic surface-active agent is selected from the group consisting of sucrose distearate, diglyceryl distearate, tetraglyceryl tristearate, decglyceryl decastearate, diglyceryl monostearate, hexaglyceryl tristearate, decaglyceryl pentastearate, sorbitan monostearate, sorbitan tristearate, diethylene glycol monostearate, the ester of glycerol and palmitic and stearic acids, polyoxyethylenated monostearate 2 EO containing 2 ethylene oxide units, glyceryl mono- and dibehenate and pentaerythritol tetrastearate;

wherein the hydrophilic surface-active agent is selected from the group consisting of polyoxyethylenated sorbitan monostearate 4 EO, polyoxyethylenated sorbitan tristearate 20 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO; and wherein the ionic amphilic lipid is selected from the group consisting of alkali metal salts of dicetyl phosphate, alkali metal salts of dimyristyl phosphate, alkali metal salts of cholesteryl sulphate, alkali metal salts of cholesteryl phosphate, the mono- and disodium salts of acylglutamic acids, phospholipids and alkylsulphonic derivatives of formula:

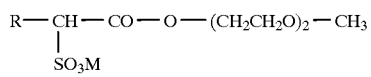

in which R represents the radicals $C_{16}H_{33}$ and $C_{18}H_{37}$, taken as a mixture or separately, and M is an alkali metal.

2. Composition according to claim 1, wherein the oily globules have a mean diameter of less than 200 nanometers.

3. Composition according to claim 1, wherein the lipophilic surface-active agent, the hydrophilic surface-active agent and the ionic amphiphilic lipid are present in an amount between 2 and 6% by weight relative to the total weight of the composition.

4. Composition according to claim 1, wherein the lipophilic surface-active agent, the hydrophilic surface-active agent and the ionic amphiphilic lipid are present in an amount between 3 and 4% by weight relative to the total weight of the composition.

5. Composition according to claim 1, wherein the lipophilic surface-active agent, the hydrophilic surface-active agent and the ionic amphiphilic lipid vary within respective ranges of 35–55%, 25–40% and 15–35% by weight, respectively relative to their total weight.

6. Composition according to claim 1, wherein the coated oily globules represent from 5 to 50% by weight relative to the total weight of the composition.

7. Composition according to claim 1, wherein the coated oily globules represent from 10 to 40% by weight relative to the total weight of the composition.

8. Composition according to claim 1, wherein the weight ratio of the oily globules to the surfactants constituting the coating is between 2 and 13.

9. Composition according to claim 1, wherein the weight ratio of the oily globules to the surfactants constituting the coating is between 6 and 8.

10. Composition according to claim 1, wherein the weight ratio of the oily globules to the surfactants constituting the coating is approximately equal to 7.

11. Composition according to claim 1, wherein the aqueous phase additionally contains one or more free or encapsulated, cosmetically or dermatologically active hydrophilic compounds.

12. Composition according to claim 11, wherein the cosmetically or dermatologically active hydrophilic compound is selected from the group consisting of short-chain alcohols and polyols.

13. Composition according to claim 11, wherein the cosmetically or dermatologically active hydrophilic compound is encapsulated in an ionic or nonionic lipid vesicle or in a nanoparticle, nanosphere, nanosponge or nanocapsule.

14. Composition according to claim 1, wherein the oily globules contain at least one fatty or lipophilic substance having a skin-care activity.

15. Composition according to claim 14, wherein the fatty or lipophilic substance is selected from the group consisting of antioxidants, free radical scavengers, moisturizing agents, melanoregulators, tanning accelerators, depigmenting agents, skin-coloring agents, liporegulators, thinning agents, anti-acne agents, antiseborrhoeic agents, anti-ageing agents, anti-wrinkle agents, anti-UV agents, keratolytic agents, anti-inflammatory agents, refreshing agents, cicatrizing agents, vascular protectors, antibacterial agents, antifungal agents, antiperspirants, deodorants, skin conditioners, immunomodulators, nutrients and essential oils and perfumes.

16. Composition according to claim 1, wherein the oily globules contain at least one fatty or lipophilic substance having a hair-care activity.

17. Composition according to claim 16, wherein the fatty or lipophilic substance is selected from the group consisting of melanoregulators, liporegulators, antiseborrhoeic agents, anti-ageing agents, anti-UV agents, keratolytic agents, antibacterial agents, antifungal agents, anti-dandruff agents, agents for combating hair loss, hair dyes, hair bleaches, reducing agents for permanent waves, hair conditioners and nutrients.

18. Composition according to claim 1, wherein the oily globules contain at least one fatty or lipophilic substance selected from the group consisting of D-α-tocopherol, DL-α-tocopherol, D-α-tocopheryl acetate, DL-α-tocopheryl acetate, ascorbyl palmitate, glycerides of vitamin F, D-vitamins, retinol, retinol esters, β-carotene, D-panthenol, farnesol, farnesyl acetate, oils rich in essential fatty acids, 5-n-octanoylsalicylic acid, salicylic acid, alkyl esters of α-hydroxy acids, asiatic acid, madecassic acid, asiaticoside, whole extract of Centella asiatica, β-glycyrrhetinic acid, α-bisabolol, ceramides, phytanetriol, sphingomyelin from milk, phospholipids of marine origin which are rich in polyunsaturated essential fatty acids, ethoxyquine, extract of romarin, extract of balm, quercetin, extract of dried microalgae, essential oil of bergamot, octyl methoxycinnamate, butylmethoxy-dibenzoylmethane, octyl triazone, yellow, brown, black and red iron oxides, titanium oxides in micrometric or nanometric form or in coated form, 3,5-di-tert-butyl-4-hydroxybenzylidene-3-camphor, 2-benzotriazol-2-yl-4-methyl-6-[3-[1,3,3,3-tetramethyl-1-[trimethylsilyl)oxy]disiloxanyl]-2-methylpropyl]phenol, perfluoro oil and hyperoxygenated corn oil.

19. Composition according to claim 1, wherein the emulsion has an oil/water ratio less than or equal to 1.

* * * * *